June 11, 1974 H. C. SWIM ET AL Plant Pat. 3,568
ROSE PLANT
Filed Feb. 12, 1973
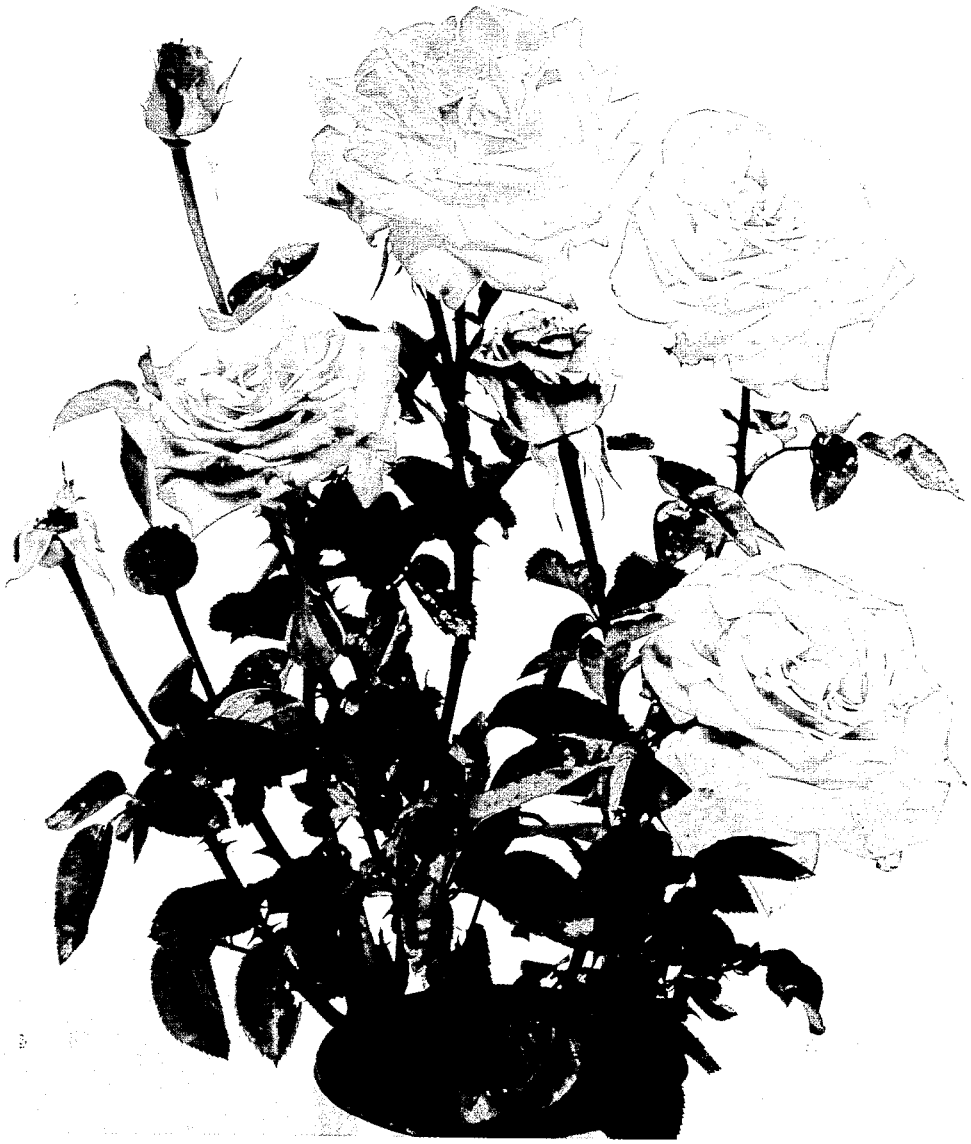

United States Patent Office

Plant Pat. 3,568

Patented June 11, 1974

3,568

ROSE PLANT

Herbert C. Swim and O. L. Weeks, Ontario, Calif., assignors to The Conard-Pyle Company, West Grove, Pa.

Filed Feb. 12, 1973, Ser. No. 331,512

Int. Cl. A01h *5/00*

U.S. Cl. Plt.—11 1 Claim

The present invention relates to a new and distinct variety of rose plant of the grandiflora class, which originated as a self-pollinated seedling of an unnamed and unpatented rose seedling which was originated by us by a series of crosses involving the rose varieties known as "Fred Howard" (Plant Pat. No. 1,006), "Golden Sceptor" (Plant Pat. No. 910) and "Golden Rapture #5" (Plant Pat. No. 1,413).

As the result of this breeding, we have produced a new and improved rose variety having the following unique combination of principal characteristics which are outstanding therein and which distinguish the same from its unnamed seedling parent, as well as from all other rose varieties of which we are aware:

(1) Abundant dark green foliage which has above average resistance to powdery mildew;
(2) A habit of bearing about half of its blooms on strong stems of single cutting length, and the remainder of the blooms being borne in clusters of three to five on stems of long cutting length;
(3) A habit of both the single and cluster blooms remaining erect at all times on the stems;
(4) A distinctive, attractive and unusual flower color which is predominantly strong reddish orange, but with some deep purplish pink coupled with a strong purplish red blend as the flowers progress to their fully open stage; and
(5) A pleasing and strong tea fragrance of the flowers.

In comparison with its unnamed seedling parent, our new variety is more closely related to the grandiflora class than the parent which tended to have more single stem blooms; its stems are more thorny and the thorns are larger than those of the seedling parent variety; the foliage is deeper green in color, heavier, more leathery and more abundant than the foliage of the parent aforesaid; and the blooms have from twelve to fifteen more petals and are more fragrant than the blooms of the parent variety.

Asexual reproduction of our new rose variety by budding, as performed at Ontario, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Hardy; bush; outdoor; seedling; for cut flowers and for garden decoration.
Class: Hybrid grandiflora.
Parentage: A seedling of a self-pollinated unnamed seedling of "Fred Howard" × "Golden Scepter" × "Golden Rapture #5."
Propagation: Holds its distinguishing characteristics through succeeding propagations by budding.

FLOWER

Locality where grown and observed: Ontario, Calif.
Flowers borne: Both singly and in clusters of from 3 to 5 to stem; on strong stems of medium length.
Quantity of bloom: Free and abundant, both outdoors and in greenhouse.
Continuity: From intermittent to continuous.
Fragrance: Strong.
*Nature.*—Tea.
Bud:
*Peduncle.*—Short; medium caliper; erect; stiff, entirely smooth.
*Before calyx breaks.*—Size—Medium. Form—Short; oval; with foliaceous appendages on the surface of the bud; with slender bristle-like foliaceous parts extending beyond the tip of the bud equal to ¼ of its length.
*As calyx breaks.*—Between Dark Reddish Orange, Hue 7.5 R 4/11 and a mixture of Strong Reddish Orange, Hue 10 R 5/11 and Strong Reddish Orange, Hue 10 R 6/12, but brighter.
*As first petal opens.*—Size—From small to medium. Form—Short; ovoid. Color—Outside—Between Vivid Yellow, Hue 2.5 Y 8/12 and Vivid Greenish Yellow, Hue 7.5 Y 8/12, blending upward into Dark Reddish Orange, Hue 7.5 R 4/11 and Strong Reddish Orange, Hue 10 R 5/11 with a touch of Moderate Red, Hue 2.5 R 4/10. Inside—Between Vivid Yellow, Hue 5 Y 8/12 and Vivid Greenish Yellow, Hue 7.5 Y 8/12 at base, blending upward into Strong Reddish Orange, Hue 10 R 6/12.
*Opening.*—Opens up well.
Bloom:
*Size (when fully open).*—Medium; from 2½ inches to 4 inches.
*Petalage.*—Very double; from 40 to 48 petals; arranged regularly.
*Form.*—Somewhat cupped, full and high-centered at first and remaining high-centered; petals being at first tightly rolled inward, but later becoming loosely cupped and rolled outward at maturity.
Petals:
*Texture.*—Fairly thick.
*Appearance.*—Inside—Satiny. Outside—Satiny.
*Shape.*—Outside—Mostly round, with apex flat and usually with 1 notch. Intermediate—Mostly round, with apex flat and usually with 1 notch. Inside—Mostly round, with apex flat.

This description of a newly opened flower was made from a rose grown outdoors during the month of October at Ontario, Calif.

*Color.*—Outer petal—Outside surface—Between Vivid Greenish Yellow, Hue 7.5 Y 8/12 and Brilliant Greenish Yellow, Hue 7.5 Y 9/8 at base, blending into a variation of Strong Purplish Red, Hue 10 RP 5/12 and Deep Pink, Hue 10 RP 6/12, with a further blending into Strong Purplish Red, Hue 10 RP 4/12; inside surface—Vivid Greenish Yellow, Hue 7.5 Y 8/12 at base, blending into a variation of Strong Reddish Orange, Hue 10 R 6/12, but somewhat lighter, and Strong Purplish Pink, Hue 5 RP 7/9, with a further blending into Strong Purplish Red, Hue 10 RP 5/12, but a little brighter. Intermediate petal—Outside surface—Between Vivid Greenish Yellow, Hue 7.5 Y 8/12 and Brilliant Greenish Yellow, Hue 7.5 Y 9/8 at base, blending into a shade between Strong Reddish Orange, Hue 7.5 R 6/12 and Strong Yellowish Pink, Hue 7.5 R 7/9; inside surface—Between vivid Yellow, Hue 5 Y 8/12 and Vivid Greenish Yellow, Hue 7.5 Y 8/12 at base, blending into Strong Orange, Hue 5 YR 7/11, with a further blending into Strong Purplish Pink, Hue 5 RP 7/9 and Strong Purplish Red, Hue 7.5 RP 5/12, but with more brilliance. Inner petal—Outside surface—Between Vivid Greenish Yellow, Hue 7.5 Y 8/12 and Brilliant Greenish Yellow, Hue 7.5 Y 9/8 at base, blending into a shade between Strong Reddish Orange, Hue 7.5 R 5/13 and Strong Reddish Orange, Hue 7.5 R 6/12, with a slight overtone of purplish orange; inside surface—Vivid Greenish Yellow, Hue 7.5 Y 8/12 at base, blending into a shade between Strong Orange, Hue 2.5 YR 6/12, and Strong Orange, Hue 2.5 YR 7/10, with a small purplish overtone at the petal tip.

This description was made from a rose that was open for three days outdoors during the month of October at Ontario, Calif.

*Color.*—Outer petal—outside surface—Brilliant Greenish Yellow, Hue 7.5 Y 9/8 at base, blending into Strong Purplish Pink, Hue 7.5 RP 7/10, and further blending into Deep Purplish Pink, Hue 7.5 RP 6/12; inside surface—between Vivid Yellow, Hue 5 Y 8/12 and Brilliant Yellow, Hue 5 Y 9/9 at base, blending into a shade a little lighter than Deep Purplish Pink, Hue 7.5 RP 6/12 with a further blending into a somewhat mottled Strong Purplish Red, Hue 7.5 RP 4/11, but a little brighter. Inner petal—Outside surface—Between Vivid Yellow, Hue, 2.5 Y 8/12 and Brilliant Yellow, Hue 2.5 Y 9/9 at base, blending into Strong Purplish Pink, Plate 7.5 RP 7/10, with a further blending at the petal tip, with a shade between Strong Purplish Red, Hue 7.5 RP 4/11 and Strong Purplish Red, Hue 7.5 RP 5/12; inside surface—Vivid Yellow, Hue 2.5 Y 8/12 at base, blending into a shade between Strong Orange, Hue 2.5 YR 6/12 with streaks of more orange and Strong Purplish Pink, Hue 7.5 RP 7/10, but somewhat lighter, with a further blending into Strong Purplish Red, Hue 7.5 RP 4/11 at the center of the petal tip, but somewhat darker.

*General color effect.*—Newly opened flower—Strong Reddish Orange, Hue 7.5 R 5/13, blending with a Strong Reddish Orange, Hue 10 R 6/12, with a further blending into variegated shades of Deep Purplish Pink, Hue 7.5 RP 6/12 and Strong Purplish Red, Hue 7.5 R 5/12. 3-days open—Strong Purplish Red, Hue 7.5 RP 4/11, blending into a Strong Reddish Orange, Hue 10 R 6/12, but brighter.

*Behavior.*—Persist; somewhat fading brown.

Flower longevity—On bush in garden—4 or 5 days in October. Cut roses grown outdoors and kept at living room temperatures—5 or 6 days in October.

REPRODUCTIVE ORGANS

Stamens: Many; arranged regularly about pistils; tucked in calyx.

Filaments: Medium length; most with anthers.

*Color.*—Reddish.

Pollen: Moderate quantity.

*Color.*—Golden yellow.

Pistils: Many.

Styles: Uneven; short; thin caliper; bunched; columnar.

Stigma:

*Color.*—Yellow.

Ovaries: All enclosed in calyx.

Hips: None observed.

Sepals: Permanent; moderately long; spear-shaped; recurved.

*Color (outside).*—A blend of red and green.

Seeds: None observed.

PLANT

Foliage:

*Leaves.*—Compound of 3 to 5 leaflets; moderately abundant; medium size; moderately heavy and leathery.

*Leaflets.*—Many. Shape — Ovate. Apex — Obtuse. Base—Round. Margin—Coarsely serrate.

*Color.*—Mature—Upper surface—Dark green; under surface—Light green. Young—Upper surface—From bronze to red, with some green overtones; under surface—blend of green and light red.

*Rachis (the supporting stem of the compound leaf).*—Medium weight. Upper side—Lightly grooved; under side—moderately prickly.

*Stipules.*—Moderately long; moderately wide; with points of medium length turning out at an angle of more than 45°.

Disease and insect resistance: Somewhat above normal resistance to both mildew and red spider, with average resistance to other usual rose diseases, as determined by comparison with other rose varieties grown under the same conditions at Ontario, Calif.

Growth:

*Habit.*—Fairly tall; upright; much-branched.

*Growth.*—Very free; vigorous.

*Canes.*—From medium to heavy caliper.

*Main stems.*—Color—Dull green. Large prickles—Several, long, straight, with long, narrow to broad base; color—light brown. Small prickles—Few; color—Brown. Hairs—None.

*Branches.*—Color—Dull green. Large prickles—Several; long; straight; with long, narrow to broad base; color—light tan, with hint of red at base. Small prickles—Few; color—Brown. Hairs—None.

*New shoots.*—Color—Reddish. Large prickles—Several; medium long; straight but hooked slightly downward; with long, narrow to broad base; color—Red. Small prickles—Several; color—Reddish. Hairs—From none to few.

We claim:

1. A new and distinct variety of rose plant of the grandiflora class, substantially as herein shown and described, characterized particularly as to novelty by the unique combination of abundant dark green foliage which has above average resistance to powdery mildew, a habit of bearing about half of its blooms on strong stems of single cutting length, and the remainder of the blooms being borne in clusters of three to five on stems of long cutting length, a habit of both the single and cluster blooms remaining erect at all times on the stems, a distinctive, attractive and unusual flower color which is predominantly strong reddish orange, but with some deep purplish pink coupled with a strong purplish red blend as the flowers progress to their fully open stage, and a pleasing and strong tea fragrance of the flowers.

No references cited.

ROBERT E. BAGWILL, Primary Examiner